US010472302B2

(12) United States Patent
Lee et al.

(10) Patent No.: US 10,472,302 B2
(45) Date of Patent: *Nov. 12, 2019

(54) LIGAND COMPOUND, ORGANIC CHROMIUM COMPOUND, CATALYST SYSTEM FOR OLIGOMERIZATION OF OLEFINS, AND METHOD FOR OLIGOMERIZATION OF OLEFINS USING THE CATALYST SYSTEM

(71) Applicant: LG CHEM, LTD., Seoul (KR)

(72) Inventors: Yong Ho Lee, Daejeon (KR); Eun Ji Shin, Daejeon (KR); Jin Young Park, Daejeon (KR); Seok Pil Sa, Daejeon (KR); Ki Soo Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/302,840

(22) PCT Filed: Jun. 18, 2015

(86) PCT No.: PCT/KR2015/006199
§ 371 (c)(1),
(2) Date: Oct. 7, 2016

(87) PCT Pub. No.: WO2015/194887
PCT Pub. Date: Dec. 23, 2015

(65) Prior Publication Data
US 2017/0029346 A1    Feb. 2, 2017

(30) Foreign Application Priority Data

Jun. 18, 2014  (KR) .................. 10-2014-0074370
Dec. 15, 2014  (KR) .................. 10-2014-0180749

(51) Int. Cl.
| | |
|---|---|
| C07C 2/00 | (2006.01) |
| C07C 2/32 | (2006.01) |
| C07F 9/02 | (2006.01) |
| C08F 4/22 | (2006.01) |
| C08F 10/00 | (2006.01) |
| B01J 31/14 | (2006.01) |
| B01J 31/24 | (2006.01) |
| C07F 9/46 | (2006.01) |
| C07F 11/00 | (2006.01) |

(52) U.S. Cl.
CPC .............. *C07C 2/32* (2013.01); *B01J 31/143* (2013.01); *B01J 31/24* (2013.01); *C07F 9/02* (2013.01); *C07F 9/46* (2013.01); *C07F 11/00* (2013.01); *C08F 4/22* (2013.01); *C08F 10/00* (2013.01); *B01J 2231/20* (2013.01); *B01J 2531/007* (2013.01); *B01J 2531/62* (2013.01); *C07C 2531/14* (2013.01); *C07C 2531/22* (2013.01)

(58) Field of Classification Search
None
See application file for complete search history.

(56) References Cited

U.S. PATENT DOCUMENTS

| | | | |
|---|---|---|---|
| 7,141,633 B2 | 11/2006 | Wass | |
| 7,786,336 B2 | 8/2010 | Zhang et al. | |
| 7,829,749 B2 | 11/2010 | Gao et al. | |
| 7,964,763 B2 | 6/2011 | Dixon et al. | |
| 8,076,523 B2 | 12/2011 | Bollmann et al. | |
| 8,309,779 B2 | 11/2012 | Han et al. | |
| 2008/0027188 A1 | 1/2008 | Small et al. | |
| 2008/0207857 A1* | 8/2008 | Small ............... | B01J 31/143 526/172 |
| 2011/0282016 A1 | 11/2011 | Carter et al. | |
| 2012/0172645 A1 | 7/2012 | Sydora | |

FOREIGN PATENT DOCUMENTS

| | | |
|---|---|---|
| CN | 1651142 A | 8/2005 |
| CN | 101032695 A | 9/2007 |
| CN | 101450326 A | 6/2009 |
| CN | 102107146 A | 6/2011 |
| CN | 103044181 A | 4/2013 |
| CN | 103285926 A | 9/2013 |
| EP | 1401890 B1 | 12/2010 |
| EP | 2955188 A1 | 12/2015 |
| JP | 2013-515601 A | 5/2013 |
| KR | 10-2004-0089446 A | 10/2004 |
| KR | 10-2006-0002742 A | 1/2006 |
| KR | 10-2008-0074339 A | 8/2008 |
| KR | 10-1311122 B1 | 9/2013 |
| KR | 10-2013-0142151 A | 12/2013 |
| KR | 10-2014-0063346 A | 5/2014 |

(Continued)

OTHER PUBLICATIONS

Sarcher et al, J. Organometallic Chem., 751, 343-350 (Year: 2014).*
Tao Jiang et al, Preparation of 1-octene by ethylene tetramerization with high selectivity, Chinese Science Bulletin, 2006, vol. 51, No. 5, pp. 521-523.
Kevin Blann et al., Ethylene tetramerisation: Subtle effects exhibited by N-substituted diphosphinoamine ligands, Journal of Catalysis, 2007, vol. 249, No. 2, pp. 244-249.
Bahattin Gumgum et al., Synthesis, characterization, crystal and molecular structure of diphenyloxophosphinoethylenediamines, Polyhedron 25 (2006) 3133-3137.
Tobias Mayer et al., Combining two coordinatively unsaturated diruthenium cores by the tetradentate ligand (Ph2P)2NCH2C6H4CH2N(PPh2)2, Journal of Organometallic Chemistry, 2012, vol. 715, pp. 64-68 .
Bernd H. Muller et al., Synthesis and Reactions of the Homoleptic Chromium(II) Bis-amide [Ph2PN(iPr)P(Ph)N(iPr)-]2Cr with Relevance to a Selective Catalytic Ethene Trimerization System to 1-Hexene, Organometallics, 2012, vol. 31, No. 9, pp. 3695-3699.

(Continued)

Primary Examiner — Yun Qian
(74) Attorney, Agent, or Firm — Dentons US LLP

(57) ABSTRACT

The present invention relates to a ligand compound, a catalyst system for oligomerization of olefins, and a method for oligomerization of olefins using the catalyst system. The catalyst system for oligomerization of olefins according to the present invention not only has excellent catalytic activity, but also exhibits high selectivity to 1-hexene or 1-octene, thus enabling more efficient preparation of alpha-olefin.

4 Claims, No Drawings

(56) References Cited

FOREIGN PATENT DOCUMENTS

| KR | 10-2015-0058049 A | 5/2015 |
| WO | 2015/046965 A1 | 4/2015 |

OTHER PUBLICATIONS

Christian Sarcher et al., Bi-and tetrametallic complexes of the noble metals with PNP-ligands, Journal of Organometallic Chemistry, 2014, vol. 751, pp. 343-350.

Baojun Zhang et al., Chromium-based Catalyst for Ethylene Tetramerization to 1-octene, Advanced Materials Research, 2012, vol. 347-353 pp. 3392-3395.

Tao Jiang et al., Ethylene tetramerization with a highly active and long-lifetime trinuclear diphenylphosphinoamine/Cr (III)/MAO catalyst, Chinese Science Bulletin, 2012, vol. 57, No. 13, pp. 1510-1515.

Osman Akba et al., Synthesis and characterizations of N,N,N',N'-tetrakis (diphenylphosphino_ethylendiamine derivatives: Use of palladium(II) complex as pre-catalyst in Suzuki coupling and Heck reactions, Journal of Organometallic Chemistry, 2009, vol. 694, No. 5, pp. 731-736.

Kirsty G. Gaw et al., Facile syntheses of new multidentate (phosphino)amines: X-ray structure of 1,4-{(OC)4Mo(Ph2P)2NCH2}2C6H4, Journal of Organometallic Chemistry, 2002, vol. 664, No. 1-2, pp. 294-297.

Ghisolfi, et al. : "Combined Experimental and Theoretical Study of Bis(diphenylphosphino)(N-thioether)amine-Type Ligands in Nickel(II) Complexes for Catalytic Ethylene Oligomerization", XP055377662, American Chemical Society, Organometallics, vol. 33, No. 10, May 27, 2014, pp. 2523-2534.

C. Kayan et al. "Synthesis and reactivity of bis(diphenylphophino) amine ligands and their application in Suzuki cross-coupling reactions," Inorganica Chimica Acta , 2012, vol. 385, pp. 164-169.

\* cited by examiner

LIGAND COMPOUND, ORGANIC CHROMIUM COMPOUND, CATALYST SYSTEM FOR OLIGOMERIZATION OF OLEFINS, AND METHOD FOR OLIGOMERIZATION OF OLEFINS USING THE CATALYST SYSTEM

CROSS-REFERENCE TO RELATED APPLICATION

This application is a National Stage Application of International Application No. PCT/KR2015/006199, filed on Jun. 18, 2015, and claims the benefit of Korean Patent Application No. 10-2014-0074370, filed on Jun. 18, 2014, and Korean Patent Application No. 10-2014-0180749, filed on Dec. 15, 2014, the contents f which are incorporated herein by reference in their entirety for all purposes as if fully set forth below.

TECHNICAL FIELD

The present invention relates to a ligand compound, an organic chromium compound, a catalyst system for oligomerization of olefins including the ligand compound or organic chromium compound, and a method for oligomerization of olefins using the catalyst system.

BACKGROUND OF ART

Linear alpha-olefin is widely used in important commercial substances such as comonomers, detergents, lubricants, plasticizers or the like, and in particular, 1-hexene and 1-octene are commonly used as comonomers for controlling density of polyethylene during preparation of linear low density polyethylene (LLDPE).

Such linear alpha-olefins have been mostly prepared through a Shell higher olefin process. However, since the method synthesizes alpha-olefins of various lengths together according to Schultz-Flory distribution, there is an inconvenience of needing an additional separation process in order to obtain a specific alpha-olefin.

In order to resolve this problem, a method of selectively synthesizing 1-hexene through a trimerization reaction of ethylene and a method of selectively synthesizing 1-octene through tetramerization of ethylene have been suggested. Further, various studies on catalysts enabling such selective oligomerization of ethylene have been undertaken.

DETAILED DESCRIPTION OF THE INVENTION

Technical Problem

It is an object of the invention to provide a novel ligand compound that enables realization of high catalytic activity and selectivity in the oligomerization reaction of olefins.

It is another object of the invention to provide a novel organic chromium compound that enables realization of high catalytic activity and selectivity in the oligomerization reaction of olefins.

It is still another object of the invention to provide a catalyst system for oligomerization of olefins including the ligand compound or organic chromium compound.

It is still another object of the invention to provide a method for oligomerization of olefins using the catalyst system.

Technical Solution

According to the present invention, a ligand compound including two or more groups represented by the following Chemical Formula 1 in a molecule, and a linker connecting between each group represented by Chemical Formula 1 by 4 to 7 carbon-carbon bonds, wherein the linker consists of a C5-20 aliphatic group, or consists of a C1-20 aliphatic group bonded with a C6-20 aromatic group, and at least one end of the linker is unsubstituted or substituted with a C6-20 aryl group, provided that if the linker consists of a C5-20 aliphatic group, at least one end thereof is substituted with a C6-20 aryl group:

[Chemical Formula 1]

(in Chemical Formula 1,

N is nitrogen, each X is independently phosphorous (P), arsenic (As), or antimony (Sb), and each of $R^1$ to $R^4$ is independently a hydrocarbyl group or a heterohydrocarbyl group)

is provided.

Further, according to the present invention, an organic chromium compound including two or more groups represented by the following Chemical Formula 3 in a molecule, and a linker connecting between each group represented by Chemical Formula 3 by 4 to 7 carbon-carbon bonds, wherein the linker consists of a C5-20 aliphatic group, or consists of a C1-20 aliphatic group bonded with a C6-20 aromatic group, and at least one end of the linker is unsubstituted or substituted with a C6-20 aryl group, provided that if the linker consists of a C5-20 aliphatic group, at least one end thereof is substituted with a C6-20 aryl group:

[Chemical Formula 3]

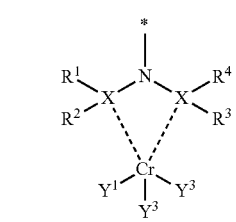

(in Chemical Formula 3,

N is nitrogen, each X is independently phosphorous (P), arsenic (As), or antimony (Sb), each of $R^1$ to $R^4$ is independently a hydrocarbyl group or a heterohydrocarbyl group, Cr is chromium, and each of $Y^1$, $Y^2$, and $Y^3$ is independently a halogen, hydrogen, a C1-0 hydrocarbyl group, or a C1-0 heterohydrocarbyl group)

is provided.

In addition, according to the present invention, a catalyst system for oligomerization of olefins including i) a chromium source, the ligand compound, and a cocatalyst, or ii) the organic chromium compound and a cocatalyst, is provided.

Further, according to the present invention, a method for oligomerization of olefins, including the step of conducting an oligomerization reaction of olefins in the presence of the catalyst system to form alpha-olefins, is provided.

Hereinafter, the ligand compound, the organic chromium compound, the catalyst system for oligomerization of olefins, and the method for oligomerization of olefins using the catalyst system will be explained in detail.

Technical terms in the present specification are only for mentioning specific embodiments, and they are not intended to restrict the present invention unless there is a particular mention about them. The singular expressions used herein may include the plural expressions unless they are differently expressed contextually. The meaning of the term "include" used in the specification embodies specific characteristics, areas, essences, steps, actions, elements, and/or components, and does not exclude existence or addition of other specific characteristics, areas, essences, steps, actions, elements, components, and/or groups.

In the present specification, 'catalyst system' means what can be obtained as the catalyst composition having activity by mixing 3 components including a chromium source, a ligand compound, and a cocatalyst, or alternatively 2 components of an organic chromium compound and a cocatalyst, at the same time or in an arbitrary order. Said 3 components or 2 components of the catalyst system may be mixed in the presence or absence of a proper solvent and a monomer, and may be used in the form of being supported or unsupported.

I. Ligand Compound

According to one embodiment of the invention, the ligand compound including two or more groups represented by the following Chemical Formula 1 in the molecule, and a linker connecting between each group represented by Chemical Formula 1 by 4 to 7 carbon-carbon bonds, wherein the linker consists of a C5-20 aliphatic group, or consists of a C1-20 aliphatic group bonded with a C6-20 aromatic group, and at least one end of the linker is unsubstituted or substituted with a C6-20 aryl group, provided that if the linker consists of a C5-20 aliphatic group, the at least one end is substituted with a C6-20 aryl group:

[Chemical Formula 1]

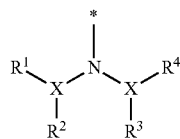

(in Chemical Formula 1,

N is nitrogen, each X is independently phosphorous (P), arsenic (As), or antimony (Sb), and each of $R^1$ to $R^4$ is independently a hydrocarbyl group or a heterohydrocarbyl group)

is provided.

As the result of successive experiments of the present inventors, it is recognized that if the ligand compound fulfilling the above requirements is applied for a catalyst system for oligomerization of olefins, it not only exhibits excellent catalytic activity, but also exhibits high selectivity to 1-hexene or 1-octene, thus enabling more effective preparation of alpha-olefins.

According to the embodiment of the invention, the ligand compound includes two or more groups represented by Chemical Formula 1 (particularly, diphosphino aminyl moiety) in the molecule, and has a linker connecting between each group represented by Chemical Formula 1 by 4 to 7, or 4 to 6, or 4 to 5, or 4 successive carbon-carbon bonds.

Herein, the expression "connecting between each group represented by Chemical Formula 1 by 4 to 7 carbon-carbon bonds" means that 4 to 7 successive carbon-carbon bonds (or 5 to 8 carbon atoms) are included at the shortest distance from any group represented by Chemical Formula 1 to another group, as illustrated below.

Each carbon-carbon bond may independently be a single bond or a double bond.

In the following example, a group represented by Chemical Formula 1 is represented by A or A' for convenience, and the A and A' may be identical to or different from each other.

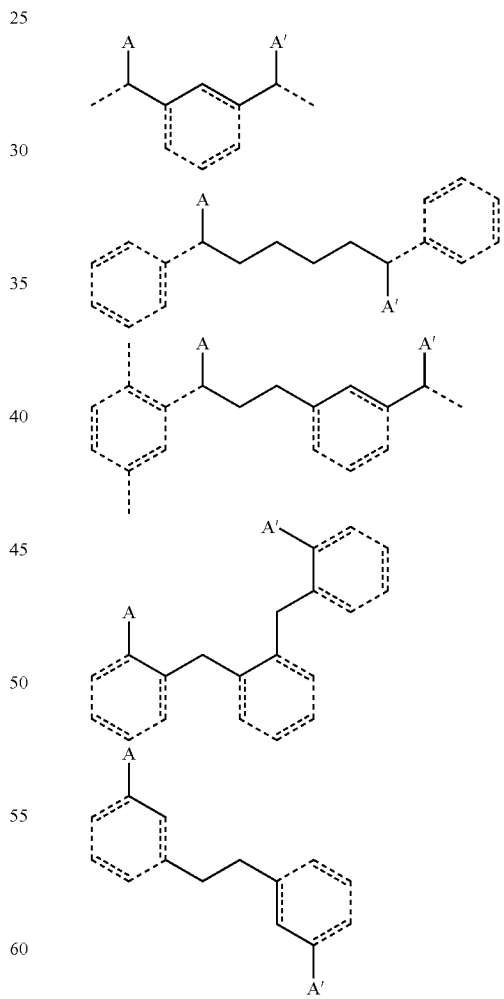

The ligand compound fulfilling the above structure may be applied to a catalyst system for oligomerization of olefins to enable active interactions between each group represented by Chemical Formula 1 and an adjacent chromium active site, thus allowing it to exhibit high oligomerization reaction activity and high selectivity to 1-hexene, 1-octene, and the like.

To the contrary, in the case of compounds that do not fulfill the above requirements, for example, compounds having one group represented by Chemical Formula 1, or compounds having a linker connecting between nitrogen atoms of two or more groups represented by Chemical Formula 1 by carbon-carbon bonds of less than 4 or greater than 7, the interactions between the group represented by Chemical Formula 1 and the chromium active site may be poor, and thus catalytic activity may be lowered or selectivity to 1-hexene or 1-octene may be lowered.

Meanwhile, according to the embodiment of the invention, in Chemical Formula 1, each X may independently be phosphorus (P), arsenic (As), or antimony (Sb). Preferably, the group represented by Chemical Formula 1 may be a diphosphino aminyl moiety wherein each X is phosphorous (P).

In Chemical Formula 1, each of $R^1$ to $R^4$ may independently be a hydrocarbyl group or a heterohydrocarbyl group. As non-limiting examples, each of $R^1$ to $R^4$ may independently be a substituted or unsubstituted C1-10 alkyl group, a substituted or unsubstituted C4-10 cycloalkyl group, a substituted or unsubstituted C6-15 aryl group, a substituted or unsubstituted C7-15 arylalkyl group, or a substituted or unsubstituted C1-10 alkoxy group.

Herein, at least one hydrogen included in the alkyl group, cycloalkyl group, aryl group, arylalkyl group and alkoxy group may be substituted with a C1-10 alkyl group, a C1-10 alkoxy group, a halogen atom, or a cyano group.

Preferably, each of $R^1$ to $R^4$ may independently be a methyl, ethyl, propyl, propenyl, propynyl, butyl, cyclohexyl, 2-methylcyclohexyl, 2-ethylcyclohexyl, 2-isopropylcyclohexyl, benzyl, phenyl, tolyl, xylyl, o-methylphenyl, o-ethylphenyl, o-isopropyl phenyl, o-t-butyl phenyl, o-methoxyphenyl, o-isopropoxyphenyl, m-methyl phenyl, m-ethyl phenyl, m-isopropyl phenyl, m-t-butyl phenyl, m-methoxyphenyl, o-isopropoxyphenyl, p-methylphenyl, p-ethylphenyl, p-isopropylphenyl, p-t-butylphenyl, p-methoxyphenyl, p-isopropoxyphenyl, cumyl, mesityl, biphenyl, naphthyl, anthracenyl, methoxy, ethoxy, phenoxy, tolyloxy, dimethylamino, thiomethyl, or trimethylsilyl group.

The ligand compound includes a linker connecting between two or more groups represented by Chemical Formula 1 by 4 to 7 carbon-carbon bonds.

Herein, the expression "connecting between each of two or more groups by 4 to 7 carbon-carbon bonds" means that 4 to 7 carbon-carbon bonds (or 5 to 8 carbon atoms) are included at the shortest distance from one group represented by Chemical Formula 1 to another group.

That is to say, the whole structure making up the linker is not specifically limited as long as the number of carbon-carbon bonds placed at the shortest distance is 4 to 7.

Specifically, the linker may consist of a C5-20 aliphatic group, for example, an alkylene group or an alkenylene group, and more specifically, it may consist of a C5-15 or a C5-10 linear or branched alkylene group or alkenylene group.

The linker may consist of a group wherein a C1-20 aliphatic group is bonded with a C6-20 aromatic group, and more specifically, the linker may consist of a group wherein one or more of a C1-20, C1-10, or C1-5 linear or branched alkylene group or alkenylene group (for example, one or two alkylene groups or alkenylene groups) is bonded with one or more of a C6-20 or C6-10 arylene group (for example, one or two arylene groups), wherein the C6-10 arylene group may be unsubstituted or additionally substituted with a C1-5 alkyl group.

At least one end of the linker (for example, one end of the linker to which the compound of Chemical Formula 1 is bonded) may be unsubstituted or substituted with a C6-20 or C6-10 aryl group. Particularly, if the linker consists of a C5-20 aliphatic group, at least one end thereof is substituted with a C6-20 aryl group, and such an aryl group may be unsubstituted or additionally substituted with a C1-5 alkyl group.

Meanwhile, according to the embodiment of the invention, a ligand compound that has two groups represented by Chemical Formula 1 in the molecule, and is represented by the following Chemical Formula 2, is provided.

[Chemical Formula 2]

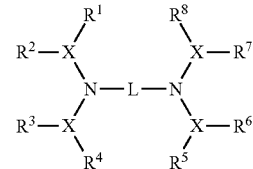

In Chemical Formula 2,
L is the linker,
each X is independently phosphorous (P), arsenic (As), or antimony (Sb), and
each of $R^1$ to $R^8$ is independently a hydrocarbyl group or a heterohydrocarbyl group.

The ligand compound represented by Chemical Formula 2 is one example of the compound having two groups represented by Chemical Formula 1 in the molecule.

In Chemical Formula 2, each X may independently be phosphorus (P), arsenic (As), or antimony (Sb), preferably phosphorus (P).

In Chemical Formula 2, each of $R^1$ to $R^8$ is independently a hydrocarbyl group or a heterohydrocarbyl group, and as non-limiting examples, may be a substituted or unsubstituted C1-10 alkyl group, a substituted or unsubstituted C4-10 cycloalkyl group, a substituted or unsubstituted C6-15 aryl group, a substituted or unsubstituted C7-15 arylalkyl group, or a substituted or unsubstituted C1-10 alkoxy group.

Herein, at least one hydrogen included in the alkyl group, cycloalkyl group, aryl group, arylalkyl group, and alkoxy group may be substituted with a C1-10 alkyl group, a C1-10 alkoxy group, and a halogen atom, or a cyano group.

Preferably, each of $R^1$ to $R^8$ may independently be a methyl, ethyl, propyl, propenyl, propynyl, butyl, cyclohexyl, 2-methylcyclohexyl, 2-ethylcyclohexyl, 2-isopropylcyclohexyl, benzyl, phenyl, tolyl, xylyl, o-methylphenyl, o-ethylphenyl, o-isopropylphenyl, o-t-butylphenyl, o-methoxyphenyl, o-isopropoxyphenyl, m-methylphenyl, m-ethylphenyl, m-isopropylphenyl, m-t-butylphenyl, m-methoxyphenyl, o-isopropoxyphenyl, p-methylphenyl, p-ethylphenyl, p-isopropylphenyl, p-t-butylphenyl, p-methoxyphenyl, p-isopropoxyphenyl, cumyl, mesityl, biphenyl, naphthyl, anthracenyl, methoxy, ethoxy, phenoxy, tolyloxy, dimethylamino, thiomethyl, or trimethylsilyl group.

According to the embodiment of the invention, the above-explained ligand compound may be a compound having the following structure. In the following examples, groups represented by Chemical Formula 1 are represented by A or A' for convenience, wherein A and A' may be identical to or different from each other.

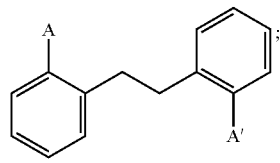
(Chemical Formula B-01)

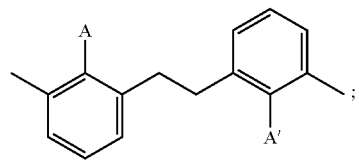
(Chemical Formula B-02)

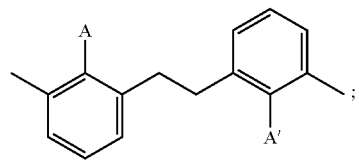
(Chemical Formula B-03)

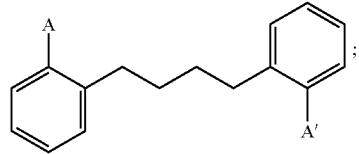
(Chemical Formula B-04)

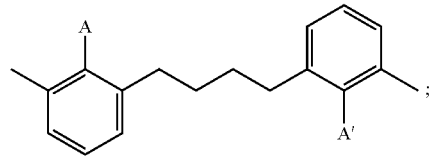
(Chemical Formula B-05)

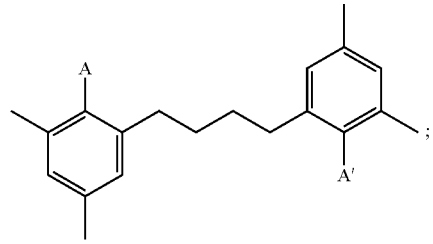
(Chemical Formula B-06)

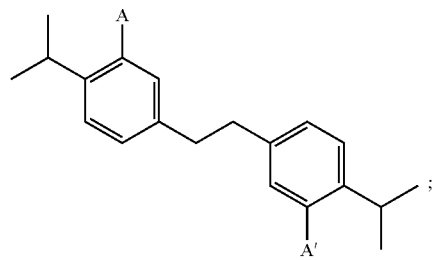
(Chemical Formula B-07)

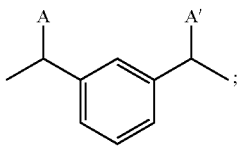
(Chemical Formula B-08)

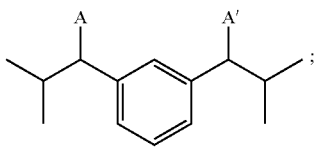
(Chemical Formula B-09)

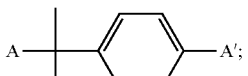
(Chemical Formula B-10)

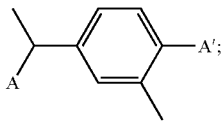
(Chemical Formula B-11)

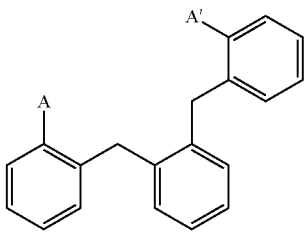
(Chemical Formula B-12)

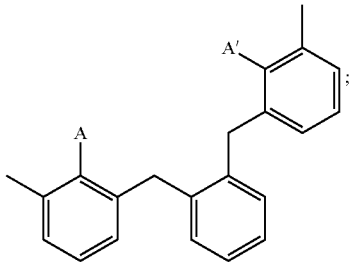
(Chemical Formula B-13)

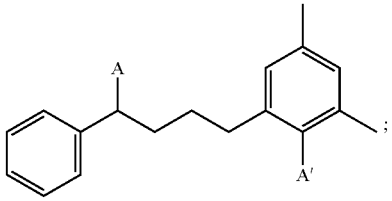
(Chemical Formula B-14)

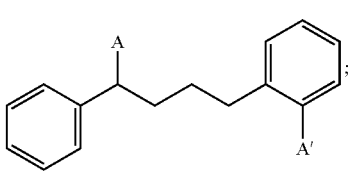
(Chemical Formula B-15)

(Chemical Formula B-16)

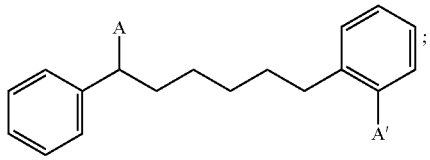

(Chemical Formula B-17)

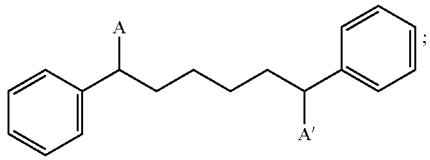

(Chemical Formula B-18)

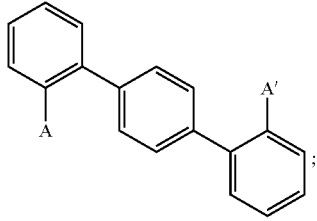

(Chemical Formula B-19)

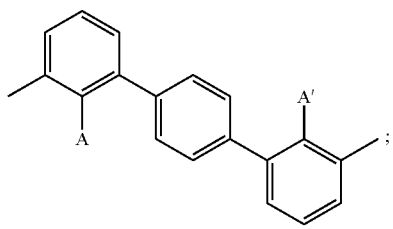

(Chemical Formula B-20)

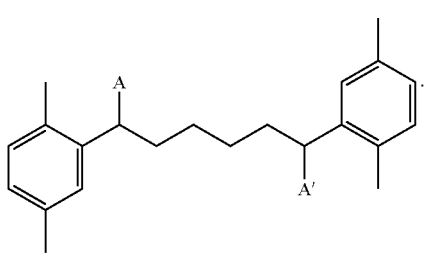

The ligand compound according to the present invention may be realized with various combinations within a range fulfilling the above-explained requirements, in addition to the above examples.

Further, the ligand compound may be synthesized by applying known reactions, and more detailed synthesis methods will be explained in the examples below.

II. Organic Chromium Compound

According to another embodiment of the invention, an organic chromium compound including two or more groups represented by the following Chemical Formula 3 in the molecule, and a linker connecting between each group represented by Chemical Formula 3 by 4 to 7 carbon-carbon bonds, wherein the linker consists of a C5-20 aliphatic group, or consists of a C1-20 aliphatic group bonded with a C6-20 aromatic group, and at least one end of the linker is unsubstituted or substituted with a C6-20 aryl group provided that if the linker consists of a C5-20 aliphatic group, at least one end thereof is substituted with a C6-20 aryl group, is provided.

[Chemical Formula 3]

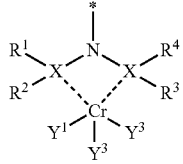

In Chemical Formula 3,

N is nitrogen, each X is independently phosphorous (P), arsenic (As), or antimony (Sb), each of $R^1$ to $R^4$ is independently a hydrocarbyl group or a heterohydrocarbyl group, Cr is chromium, and each of $Y^1$, $Y^2$, and $Y^3$ is independently hydrogen, a C1-0 hydrocarbyl group, or a C1-0 heterohydrocarbyl group.

The organic chromium compound is a chromium complex compound of the above-explained ligand compound, and has a form wherein a chromium atom included in any chromium source is coordinated with the X part of the group represented by Chemical Formula 1. Such an organic chromium compound may be applied for a catalyst system for oligomerization of olefins to exhibit excellent catalytic activity and high selectivity to 1-hexene or 1-octene.

In Chemical Formula 3, explanations regarding X and $R^1$ to $R^4$ are replaced with the explanations in Chemical Formula 1.

Further, in Chemical Formula 3, Cr is chromium, and each of $Y^1$, $Y^2$, and $Y^3$ is independently a halogen, hydrogen, a C1-10 hydrocarbyl group, or a C1-10 heterohydrocarbyl group.

The organic chromium compound of Chemical Formula 3 may be obtained by a common method of forming a chromium complex compound of the ligand compound.

III. Catalyst System for Oliaomerization of Olefins

According to still another embodiment of the invention, a catalyst system including i) a chromium source, the above-explained ligand compound, and a cocatalyst, or ii) the above-explained organic chromium compound and a cocatalyst, is provided.

That is, the catalyst system for oligomerization of olefins may be i) a three-component catalyst system including a chromium source, the above-explained ligand compound, and a cocatalyst, or ii) a two-component catalyst system including the above-explained organic chromium compound and a cocatalyst.

In the catalyst system, the chromium source may be an organic or inorganic chromium compound with an oxidation state of chromium of 0 to 6, for example, a chromium metal, or a compound wherein any organic or inorganic radical is bonded to chromium. Herein, the organic radical may be an alkyl, an alkoxy, an ester, a ketone, an amido, a carboxylate radical, and the like, which have 1 to 20 carbon atoms per radical, and the inorganic radical may be a halide, sulfate, oxide, and the like.

Preferably, the chromium source is a compound that can exhibit high activity for oligomerization of olefins and can be easily used and acquired, and may be one or more compounds selected from the group consisting of chromium (III) acetylacetonate, chromium(III) chloride tetrahydrofuran, chromium(III) 2-ethylhexanoate, chromium(III)

acetate, chromium(III) butyrate, chromium(III) pentanoate, chromium(III) laurate, chromium(III) tris(2,2,6,6-tetramethyl-3,5-heptanedionate), and chromium(III) stearate.

Preferably, the cocatalyst is an organometallic compound including a Group 13 metal, and may not be specifically limited as long as it can be generally used for polymerization of olefins in the presence of a transition metal catalyst.

For example, the cocatalyst may be one or more compounds selected from the group consisting of compounds represented by the following Chemical Formulae 4 to 6.

     [Chemical Formula 4]

In Chemical Formula 4, each $R^{41}$ is the same as or different from each other and are independently a halogen radical, a $C_1$-$C_{20}$ hydrocarbyl radical, or a $C_1$-$C_{20}$ hydrocarbyl radical substituted with a halogen, and c is an integer of 2 or more.

     [Chemical Formula 5]

In Chemical Formula 5, D is aluminum or boron, and $R^{51}$ is a $C_1$-$C_{20}$ hydrocarbyl or a $C_1$-$C_{20}$ hydrocarbyl substituted with a halogen.

     [Chemical Formula 6]

In Chemical Formula 6,

L is a neutral Lewis base, $[L-H]^+$ is a Bronsted acid, Q is boron or aluminum of a +3 oxidation state, and E is independently a $C_6$-$C_{20}$ aryl group or a $C_1$-$C_{20}$ alkyl group of which at least one hydrogen is substituted with a halogen, a $C_1$-$C_{20}$ hydrocarbyl, an alkoxy functional group, or a phenoxy functional group.

According to one embodiment, the compound represented by Chemical Formula 4 may be an alkyl aluminoxane such as methyl aluminoxane, ethyl aluminoxane, isobutyl aluminoxane, butyl aluminoxane, and the like.

According to one embodiment, the compound represented by Chemical Formula 5 may be trimethylaluminum, triethylaluminum, triisobutylaluminum, tripropylaluminum, tributylaluminum, dimethylchloroaluminum, dimethylisobutylaluminum, dimethylethylaluminum, diethylchloroaluminum, triisopropylaluminum, tri-s-butylaluminum, tricyclopentylaluminum, tripentylaluminum, triisopentylaluminum, trihexylaluminum, ethyldimethylaluminum, methyldiethylaluminum, triphenylaluminum, tri-p-tolylaluminum, dimethylaluminummethoxide, dimethylaluminumethoxide, trimethylboron, triethylboron, triisobutylboron, tripropylboron, tributylboron, and so on.

Furthermore, according to one embodiment, the compound represented by Chemical Formula 6 may be triethylammonium tetraphenylborate, tributylammonium tetraphenylborate, trimethylammonium tetraphenylborate, tripropylammonium tetraphenylborate, trimethylammonium tetra(p-tolyl)borate, tripropylammonium tetra(p-tolyl)borate, triethylammonium tetra(o,p-dimethylphenyl)borate, trimethylammonium tetra(o,p-dimethylphenyl)borate, tributylammonium tetra(p-trifluoromethylphenyl)borate, trimethylammonium tetra(p-trifluoromethylphenyl)borate, tributylammonium tetrapentafluorophenylborate, N,N-diethylanilinium tetraphenylborate, N,N-diethylanilinium tetraphenylborate, N,N-diethylanilinium tetrapentafluorophenylborate, diethylammonium tetrapentafluorophenylborate, triphenylphosphonium tetraphenylborate, trimethylphosphonium tetraphenylborate, triethylammonium tetraphenylaluminum, tributylammonium tetraphenylaluminum, trimethylammonium tetraphenylaluminum, tripropylammonium tetraphenylaluminum, trimethylammonium tetra(p-tolyl)aluminum, tripropylammonium tetra(p-tolyl) aluminum, triethylammonium tetra(o,p-dimethylphenyl) aluminum, tributylammonium tetra(p-trifluoromethylphenyl)aluminum, trimethylammonium tetra(p-trifluoromethylphenyl)aluminum, tributylammonium tetrapentafluorophenylaluminum, N, N-diethylanilinium tetraphenylaluminum, N,N-diethylanilinium tetraphenylaluminum, N,N-diethylanilinium tetrapentafluorophenylaluminum, diethylammonium tetrapentafluorophenylaluminum, triphenylphosphonium tetraphenylaluminum, trimethylphosphonium tetraphenylaluminum, triphenylcarbonium tetraphenylborate, triphenylcarbonium tetraphenylaluminum, triphenylcarbonium tetra(p-trifluoromethylphenyl)borate, triphenylcarbonium tetrapentafluorophenylborate, and so on.

Further, as non-limiting examples, the cocatalyst may be an organoaluminum compound, an organoboron compound, an organomagnesium compound, an organozinc compound, an organolithium compound, or a mixture thereof.

According to one example, the cocatalyst is preferably an organoaluminum compound, and more preferably, may be one or more compounds selected from the group consisting of trimethyl aluminum, triethyl aluminum, triisopropyl aluminum, triisobutyl aluminum, ethylaluminum sesquichloride, diethylaluminum chloride, ethyl aluminum dichloride, methylaluminoxane, and modified methylaluminoxane.

The content ratio of the components composing the catalyst system may be determined by considering the catalytic activity and the selectivity to linear alpha-olefins.

According to one embodiment, when the catalyst system is a three-component catalyst system, it is preferable that the mole ratio of the diphosphino aminyl moiety of the ligand compound: the chromium source: the cocatalyst is controlled to be about 1:1:1 to 10:1:10,000, or about 1:1:100 to 5:1:3,000.

According to one embodiment, when the catalyst system is a two-component catalyst system, it is preferable that the mole ratio of the diphosphino aminyl moiety of the organic chromium compound: the cocatalyst is controlled to be 1:1 to 1:10,000, or 1:1 to 1:5000, or 1:1 to 1:3000.

The components composing the catalyst system may be mixed at the same time or in an arbitrary order in the presence or absence of a proper solvent and a monomer for acting as an active catalyst system. The proper solvent may be heptane, toluene, cyclohexane, methylcyclohexane, 1-hexene, 1-octene, diethylether, tetrahydrofuran, acetonitrile, dichloromethane, chloroform, chlorobenzene, methanol, acetone, and so on.

Furthermore, according to one embodiment, the catalyst system may further include a supporting material. That is, the ligand compound of Chemical Formula 1 may be applied to the oligomerization of ethylene in the form of being supported on the supporting material. The supporting material may be metals, metal salts, or metal oxides which are commonly applied to a supported catalyst. For nonrestrictive examples, the supporting material may be silica, silica-alumina, silica-magnesia, and so on, and may include an oxide, a carbonate, a sulfate, or a nitrate component such as $Na_2O$, $K_2CO_3$, $BaSO_4$, $Mg(NO_3)_2$, and so on.

IV. Oliqomerization Method of Olefins Using the Catalyst System

According to still another embodiment of the invention, a method for oligomerization of olefins, including the step of carrying out the oligomerization reaction of olefins in the presence of the catalyst system to form alpha-olefins, is provided.

The method for oligomerization of olefins of the present invention may be carried out using olefins (for example, ethylene) as raw material by applying said catalyst system and a common device and contact technology.

For nonrestrictive examples, the oligomerization reaction of olefins may be carried out by a homogeneous liquid phase reaction in the presence or absence of an inert solvent, by a slurry reaction using the catalyst system that is partially or not totally dissolved, by a bulk reaction in which the alpha-olefin, the product, acts as a main medium, or by a gas phase reaction.

The oligomerization reaction of olefins may be carried out in the presence of an inert solvent. For nonrestrictive examples, the inert solvent may be benzene, toluene, xylene, cumene, chlorobenzene, dichlorobenzene, heptane, cyclohexane, methylcyclohexane, methylcyclopentane, n-hexane, 1-hexene, 1-octene, and so on.

The oligomerization reaction of olefins may be carried out at a temperature of about 0 to 200° C., about 0 to 150° C., about 30 to 100° C., or about 50 to 100° C. Furthermore, the reaction may be carried out at a pressure of about 15 to 3000 psig, or about 15 to 1500 psig, or about 15 to 1000 psig.

Advantageous Effects

The catalyst system for oligomerization of olefins has excellent catalytic activity and simultaneously exhibits high selectivity to 1-hexene or 1-octene, thus enabling more effective preparation of alpha-olefins.

DETAILED DESCRIPTION OF THE EMBODIMENTS

Hereinafter, preferable examples and comparative examples are presented for better understanding the present invention. However, the following examples are only for illustrating the present invention and the present invention is not limited to or by them.

In the following examples and comparative examples, all the reactions were progressed under argon using Schlenk technique or a glovebox. The synthesized ligands were analyzed by $^1$H (500 MHz) and $^{31}$P (202 MHz) NMR spectra using a Varian 500 MHz spectrometer. The shifts were expressed in ppm as a downfield from TMS with a residual solvent peak as a reference. The phosphorous probes were calibrated with aqueous $H_3PO_4$.

EXAMPLE 1

Synthesis of a compound C-01

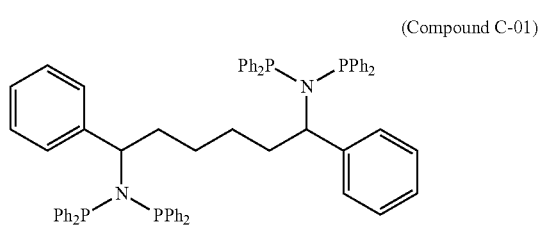
(Compound C-01)

5 mmol of 1,4-dibenzoylbutane was introduced into a 250 ml Schlenk flask that was dried and of which the interior was substituted with Ar. 25 mL (50 mmol) of a solution of 2M $NH_3$ in ethanol was added dropwise to the flask while stirring at room temperature. Under an inert atmosphere, 5.0 mL (20 mmol) of titanium(IV) isopropoxide was taken with a syringe, and added dropwise to the flask while stirring under a water bath. After the introduction was completed, the mixture was stirred overnight under a water bath.

0.6 g (15 mmol) of sodium borohydride was introduced into another flask that was dried and of which the interior was substituted with Ar, and the above-prepared reaction mixture was added thereto dropwise through a cannula under an ice bath. After the introduction was completed, the temperature of the mixture was slowly raised to room temperature, followed by stirring for 4 h or more. Under an ice bath, an aqueous solution of ammonium hydroxide (50 mmol) was slowly added dropwise to the reaction mixture to quench it. Further, it was extracted with $CHCl_3$, residual moisture of the organic layer was removed with $MgSO_4$, and then the solvent was removed under vacuum to obtain an oily reaction mixture.

The reaction mixture was separated through column chromatography with silica as a stationary phase using an eluent (MC:MeOH:$NH_4OH$=100:10:1) to obtain 0.27 g of 1,6-diphenylhexane-1,6-diamine (yield 20%).

1,6-diphenylhexane-1,6-diamine (5 mmol) and triethylamine (3-10 equiv. to amine) were dissolved in dichloromethane (80 mL) Under Ar. While the flask was immersed in a water bath, chlorodiphenylphosphine (20 mmol, 2 equiv. to amine) was slowly introduced, and the mixture was stirred overnight. After placing the mixture under vacuum to remove the solvent, THF was introduced thereto, the mixture was sufficiently stirred, and a triethylammonium chloride salt was removed with an air-free glass filter. Remaining solvent was removed from the filtrate to obtain a product (compound C-01).

$^{31}$P NMR (202 MHz, $CDCl_3$): 63.8-58.7 (br d)
$^1$H NMR (500 MHz, $CDCl_3$): 7.23-6.51 (50H, m), 3.61 (2H, m), 1.65 (2H, m), 0.70 (6H, m)

EXAMPLE 2

Synthesis of a compound C-02

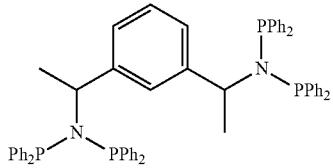
(compound C-02)

3.3 g (20 mmol) of 1,1'-(1,3-phenylene)diethanone was introduced into a 250 ml Schlenk flask that was dried and of which the interior was substituted with Ar. 100 mL (200 mmol) of a solution of 2M $NH_3$ in ethanol was added dropwise to the flask while stirring at room temperature. Under an inert atmosphere, 23.7 mL (80 mmol) of titanium (IV) isopropoxide was taken with a syringe, and added dropwise to the flask while stirring under a water bath. After the introduction was completed, the mixture was stirred overnight under a water bath.

2.3 g (60 mmol) of sodium borohydride was introduced into another flask that was dried and of which the interior was substituted with Ar, and the above-prepared reaction mixture was added thereto dropwise through a cannula under an ice bath. After the introduction was completed, the temperature of the mixture was slowly raised to room temperature, followed by stirring for 4 h or more. Under an ice bath, an aqueous solution of ammonium hydroxide (100 mmol) was slowly added dropwise to the reaction mixture to quench. Further, it was extracted with CDCl₃, residual moisture of the organic layer was removed with MgSO₄, and then the solvent was removed under vacuum to obtain 2 g (12 mmol) of oily 1,1'-(1,3-phenylene)diethanamine.

$^1$H NMR (500 MHz, CDCl₃): 7.31-7.19 (4H, m), 4.10 (2H, m), 1.58 (4H, br s), 1.37 (6H, d).

1,1'-(1,3-phenylene)diethanamine (5 mmol) and triethylamine (3-10 equiv. to amine) were dissolved in dichloromethane (80 mL) under Ar. While the flask was immersed in a water bath, chlorodiphenylphosphine (20 mmol, 2 equiv. to amine) was slowly introduced, and the mixture was stirred overnight. After placing the mixture under vacuum to remove the solvent, THF was introduced, the mixture was sufficiently stirred, and a triethylammonium chloride salt was removed with an air-free glass filter. Remaining solvent was removed in the filtrate to obtain a product (compound C-02).

$^{31}$P NMR (202 MHz, CDCl₃): 54.0 (br s), 46.1 (br s)

$^1$H NMR (500 MHz, CDCl₃): 7.7-6.9 (44H, m), 4.6-4.4 (2H, m), 1.5-1.3 (6H, m)

COMPARATIVE EXAMPLE 1

Synthesis of D-01

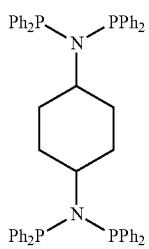

(Compound D-01)

Cyclohexane-1,4-diamine (5 mmol) and triethylamine (3-10 equiv. to amine) were dissolved in dichloromethane (80 mL) under Ar. While the flask was immersed in a water bath, chlorodiphenylphosphine (20 mmol, 2 equiv. to amine) was slowly introduced, and the mixture was stirred overnight. After placing the mixture under vacuum to remove the solvent, THF was introduced, the mixture was sufficiently stirred, and a triethylammonium chloride salt was removed with an air-free glass filter. Remaining solvent was removed in the filtrate to obtain a product (compound D-01).

$^{31}$P NMR (202 MHz, CDCl₃): 49.63 (br s), 54.77 (br s)

$^1$H NMR (500 MHz, CDCl₃): 1.15 (4H, m), 2.19 (4H, m), 3.36 (2H, m), 6.5-8.0 (40H, m)

COMPARATIVE EXAMPLE 2

Synthesis of D-02

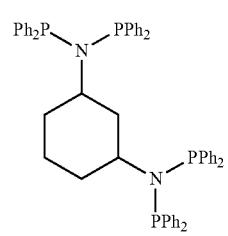

(Compound D-02)

Cyclohexane-1,3-diamine (5 mmol) and triethylamine (3-10 equiv. to amine) were dissolved in dichloromethane (80 mL) under Ar. While the flask was immersed in a water bath, chlorodiphenylphosphine (20 mmol, 2 equiv. to amine) was slowly introduced, and the mixture was stirred overnight. After placing the mixture under vacuum to remove the solvent, THF was introduced, the mixture was sufficiently stirred, and a triethylammonium chloride salt was removed with an air-free glass filter. Remaining solvent was removed in the filtrate to obtain a product (compound D-02).

$^{31}$P NMR (202 MHz, CDCl₃): 49.99 (br m)

COMPARATIVE EXAMPLE 3

Synthesis of D-03

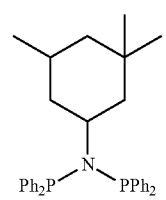

(Compound D-03)

3,3,5-trimethylcyclohexanamine (5 mmol) and triethylamine (3-10 equiv. to amine) were dissolved in dichloromethane (80 mL) under Ar. While the flask was immersed in a water bath, chlorodiphenylphosphine (20 mmol, 2 equiv. to amine) was slowly introduced, and the mixture was stirred overnight. After placing the mixture under vacuum to remove the solvent, THF was introduced, the mixture was sufficiently stirred, and a triethylammonium chloride salt was removed with an air-free glass filter. Remaining solvent was removed in the filtrate to obtain a product (compound D-03).

$^{31}$P NMR (202 MHz, CDCl₃): 45.5 (br s), 55.5 (br s)

COMPARATIVE EXAMPLE 4

Synthesis of D-04

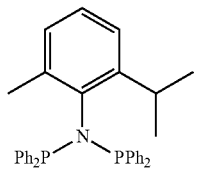

(Compound D-04)

2-isopropyl-6-methylaniline (5 mmol) and triethylamine (3-10 equiv. to amine) were dissolved in dichloromethane (80 mL) under Ar. While the flask was immersed in a water bath, chlorodiphenylphosphine (20 mmol, 2 equiv. to amine) was slowly introduced, and the mixture was stirred overnight. After placing the mixture under vacuum to remove the solvent, THF was introduced, the mixture was sufficiently stirred, and a triethylammonium chloride salt was removed with an air-free glass filter. Remaining solvent was removed in the filtrate to obtain a product (compound D-04).

$^{31}$P NMR (202 MHz, CDCl$_3$): 57.0 (br s)

$^1$H NMR (500 MHz, CDCl$_3$): 0.8 (6H), 1.6 (3H), 3.13 (1H), 7.0-7.3 (3H), 7.4-8.0 (20H)

COMPARATIVE EXAMPLE 5

Synthesis of a compound D-05

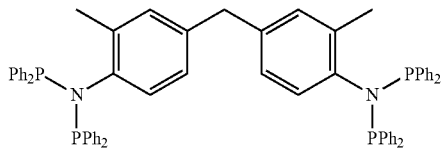

(compound D-05)

4,4'-methylenebis(2-methylaniline) (5 mmol) and triethylamine (3-10 equiv. to amine) were dissolved in dichloromethane (80 mL) under Ar. While the flask was immersed in a water bath, chlorodiphenylphosphine (20 mmol, 2 equiv. to amine) was slowly introduced, and the mixture was stirred overnight. After placing the mixture under vacuum to remove the solvent, THF was introduced, the mixture was sufficiently stirred, and a triethylammonium chloride salt was removed with an air-free glass filter. Remaining solvent was removed in the filtrate to obtain a product (compound D-05).

$^{31}$P NMR (202 MHz, CDCl$_3$): 61.7 (s)

$^1$H NMR (500 MHz, CDCl$_3$): 1.6 (6H), 3.7 (2H), 6.54 (2H), 6.75 (2H), 7.0-7.8 (42H)

EXPERIMENTAL EXAMPLE 1

(Step I)

Under an argon atmosphere, chromium(III) acetylacetonate (17.5 mg, 0.05 mmol) and the ligand compound C-01 according to Example 1 (0.025 mmol) were introduced into a flask, 100 mL of methylcyclohexane was added thereto, and the mixture was stirred to prepare a solution of 0.5 mM (based on Cr).

(Step II)

A Parr reactor with a capacity of 600 ml was placed under vacuum at 120° C. for 2 h, the interior of the reactor was substituted with argon, and the temperature was decreased to 60° C.

Thereafter, 175 mL of methylcyclohexane and 2 ml of MMAO (isoheptane solution, Al/Cr=1200) were introduced, and 5 mL of the above 0.5 mM solution (2.5 μmol of Cr) was introduced thereto.

The reaction mixture was stirred at 500 rpm for 1 min, an ethylene line valve adjusted to 60 bar was opened to fill the interior of the reactor with ethylene, the temperature was adjusted to 60° C., and the mixture was stirred at 500 rpm for 15 min.

The ethylene line valve was closed, the reactor was cooled to 0° C. using a dry ice/acetone bath, non-reacted ethylene was slowly vented, and 0.5 mL of nonane (GC internal standard) was introduced.

The reaction mixture was stirred for 10 s, 2 mL of the liquid part of the reactor was taken and quenched with water, and the obtained organic part was filtered with a PTFE syringe filter to conduct GC-FID analysis.

(Step III)

400 mL of an ethanol/HCl solution (10 vol% of aqueous 12M HCl solution) was introduced to the remaining reaction solution, and the mixture was stirred and filtered to obtain a polymer. The obtained polymer was dried in a vacuum oven at 65° C. overnight, and then the weight was measured.

EXPERIMENTAL EXAMPLE 2

The experiment was conducted by the same method as Experimental Example 1, except that the compound C-02 according to Example 2 (0.025 mmol) was used as a ligand compound instead of the compound C-01.

COMPARATIVE EXPERIMENTAL EXAMPLE 1

(Step I)

Under an argon gas atmosphere, chromium(III) acetylacetonate (17.5 mg, 0.05 mmol) and the ligand compound D-01 according to Comparative Example 1 (0.025 mmol) were introduced into a flask, 10 mL of cyclohexane was added thereto, and the mixture was stirred to prepare a solution of 5 mM (based on Cr).

(Step II)

A Parr reactor with a capacity of 600 ml was prepared, it was placed under vacuum at 120° C. for 2 h, the interior of the reactor was replaced with argon, and the temperature was decreased to 45° C.

Thereafter, 90 mL of cyclohexane and 2 ml of an MMAO (isoheptane solution, Al/Cr=1200) were introduced, and 0.5 mL (2.5 μmol of Cr) of the 5 mM solution was introduced thereto.

The reaction mixture was stirred at 500 rpm for 2 min, an ethylene line valve adjusted to 45 bar was opened to fill the interior of the reactor with ethylene, the temperature was decreased to 45° C., and the mixture was stirred at 500 rpm for 15 min.

The ethylene line valve was closed, the reactor was cooled to 0° C. using a dry ice/acetone bath, non-reacted ethylene was slowly vented, and 0.5 mL of nonane (GC internal standard) was introduced.

The reaction mixture was stirred for 10 s, 2 mL of the liquid part of the reactor was taken and quenched with water, and the obtained organic part was filtered with a PTFE syringe filter to conduct GC-FID analysis.

(Step III)

400 mL of an ethanol/HCl solution (10 vol% of aqueous 12 M HCl solution) was introduced to the remaining reaction solution, and the mixture was stirred and filtered to obtain a polymer. The obtained polymer was dried in a vacuum oven at 65° C. overnight, and then the weight was measured.

COMPARATIVE EXPERIMENTAL EXAMPLE 2

The experiment was conducted by the same method as Comparative Experimental Example 1, except that the compound D-02 according to Comparative Example 2 (0.025 mmol) was used as a ligand compound instead of the compound D-01.

COMPARATIVE EXPERIMENTAL EXAMPLE 3

The experiment was conducted by the same method as Comparative Experimental Example 1, except that the compound D-03 according to Comparative Example 3 (0.05 mmol) was used as a ligand compound instead of the compound D-01.

COMPARATIVE EXPERIMENTAL EXAMPLE 4

The experiment was conducted by the same method as Comparative Experimental Example 1, except that the compound D-04 according to Comparative Example 4 (0.05 mmol) was used as a ligand compound instead of the compound D-01.

COMPARATIVE EXPERIMENTAL EXAMPLE 5

The experiment was conducted by the same method as Experimental Example 1, except that the compound D-05 according to Comparative Example 5 (0.025 mmol) was used as a ligand compound instead of the compound C-01.

Referring to Table 1, it is confirmed that in the case of Examples, higher catalytic activities were exhibited compared to Comparative Examples, and the sums of selectivities to 1-hexene and 1-octene were high.

The invention claimed is:

1. A ligand compound comprising:
two groups represented by the following Chemical Formula 1, and a linker connecting the two groups by four to seven consecutive carbon-carbon bonds:

[Chemical Formula 1]

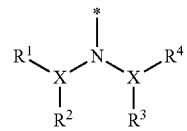

wherein in Chemical Formula 1:
each X is phosphorous (P), and
each of R1 to fC-R4 is independently a substituted or unsubstituted C1-10 alkyl group, a substituted or unsubstituted C4-10 cycloalkyl group, a substituted or unsubstituted C6-15 aryl group, a substituted or unsubstituted C7-15 arylalkyl group, or a substituted or unsubstituted C1-10 alkoxy group, and
wherein the ligand compound is any one of the compounds represented by Chemical Formulae B-01, B-02, B-07 to B-11, B-14, B-15, B-17 and B-20, wherein the two groups represented by Chemical Formula 1 are represented by A or A', and wherein A and A' are identical to or different from each other:

Chemical Formula B-01

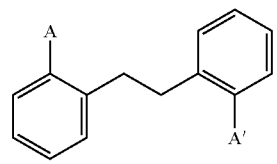

TABLE 1

|  | Ligand compound | Catalytic activity (kg/molCr/h) | alpha-olefin (wt %) | | | $1\text{-}C_{10}$ to $1\text{-}C_{40}$ | $C_6$ isomers (wt %) | Poly alpha-olefin (wt %) |
|---|---|---|---|---|---|---|---|---|
|  |  |  | $1\text{-}C_6$ and $1\text{-}C_8$ | | | | | |
|  |  |  | $1\text{-}C_6$ | $1\text{-}C_8$ | (sum) | | | |
| Experimental Example 1 | Example 1 (C-01) | 131,000 | 34.3 | 53.8 | 88.1 | 6.5 | 4.0 | 0.5 |
| Experimental Example 2 | Example 2 (C-02) | 34,300 | 21.2 | 64.2 | 85.4 | 6.0 | 5.2 | 1.6 |
| Comparative Experimental Example 1 | Comparative Example 1 (D-01) | 33,900 | 18.2 | 66.0 | 84.2 | 7.0 | 6.2 | 0.3 |
| Comparative Experimental Example 2 | Comparative Example 2 (D-02) | 30,300 | 19.2 | 66.0 | 85.2 | 7.0 | 5.2 | 0.6 |
| Comparative Experimental Example 3 | Comparative Example 3 (D-03) | 10,100 | 12.0 | 68.9 | 80.9 | 9.3 | 6.6 | 0.1 |
| Comparative Experimental Example 4 | Comparative Example 4 (D-04) | 21,000 | 27.1 | 56.3 | 83.4 | 10.1 | 3.9 | 0.5 |
| Comparative Experimental Example 5 | Comparative Example 5 (D-05) | 61,600 | 16.7 | 60.9 | 77.6 | 8.8 | 9.5 | 1.6 |

Chemical Formula B-02

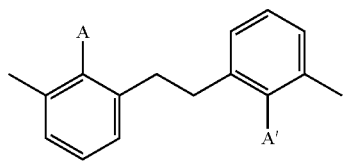

Chemical Formula B-07

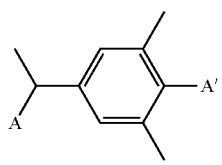

Chemical Formula B-08

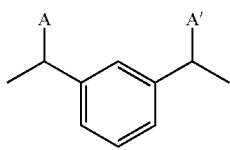

Chemical Formula B-09

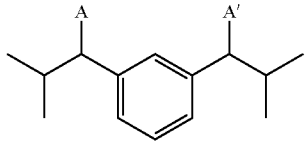

Chemical Formula B-10

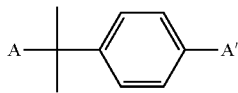

Chemical Formula B-11

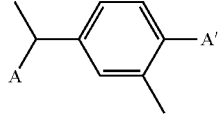

Chemical Formula B-14

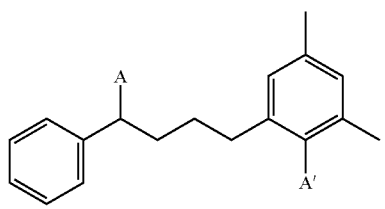

Chemical Formula B-15

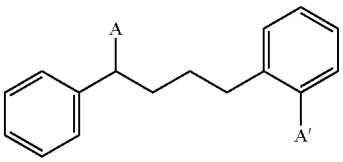

Chemical Formula B-17

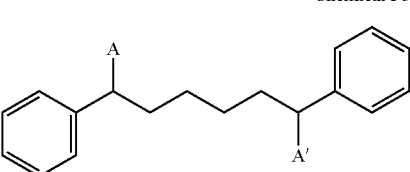

Chemical Formula B-20

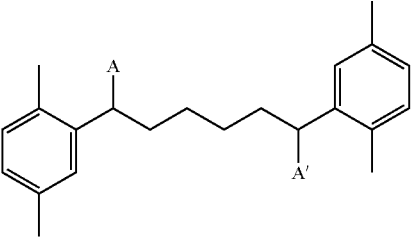

2. A catalyst system for oligomerization of olefins, comprising:
a chromium source, the ligand compound according to claim 1, and a cocatalyst.

3. The catalyst system according to claim 2, wherein the chromium source is one or more compounds selected from the group consisting of chromium(III) acetylacetonate, chromium(III) chloride tetrahydrofuran, chromium(III) 2-ethylhexanoate, chromium(III) acetate, chromium(III) butyrate, chromium(III) pentanoate, chromium(III) laurate, chromium(III) tris(2,2,6,6-tetramethyl-3,5-heptanedionate), and chromium(III) stearate.

4. The catalyst system according to claim 2, wherein the cocatalyst is one or more compound selected from the group consisting of trimethyl aluminum, triethyl aluminum, triisopropyl aluminum, triisobutyl aluminum, ethylaluminum sesquichloride, diethylaluminum chloride, ethyl aluminum dichloride, methylaluminoxane, and modified methylaluminoxane.

* * * * *